(12) United States Patent
Gateno et al.

(10) Patent No.: US 6,671,539 B2
(45) Date of Patent: Dec. 30, 2003

(54) METHOD AND APPARATUS FOR FABRICATING ORTHOGNATHIC SURGICAL SPLINTS

(75) Inventors: Jaime Gateno, Houston, TX (US); John F. Teichgraeber, Houston, TX (US); James Xia, Houston, TX (US)

(73) Assignee: Board of Regents University of Texas System, Austin, TX (US)

( * ) Notice: Subject to any disclaimer, the term of this patent is extended or adjusted under 35 U.S.C. 154(b) by 60 days.

(21) Appl. No.: 09/970,139

(22) Filed: Oct. 3, 2001

(65) Prior Publication Data
US 2003/0065259 A1 Apr. 3, 2003

(51) Int. Cl.[7] .................................................. A61B 6/00
(52) U.S. Cl. ...................... 600/426; 600/427; 433/214; 433/223; 345/630
(58) Field of Search ................................ 600/426, 427; 433/68, 69, 37, 211, 223; 382/128, 131; 345/419, 420, 629, 630, 634

(56) References Cited

U.S. PATENT DOCUMENTS

| | | | | |
|---|---|---|---|---|
| 5,823,778 | A | * 10/1998 | Schmitt et al. | 433/214 |
| 6,152,731 | A | * 11/2000 | Jordan et al. | 433/69 |
| 6,167,295 | A | * 12/2000 | Cosman | 600/426 |
| 6,266,453 | B1 | * 7/2001 | Hibbard et al. | 382/131 |
| 6,396,940 | B1 | * 5/2002 | Carrott et al. | 382/128 |

FOREIGN PATENT DOCUMENTS

BE 1011205 A3 * 6/1999

OTHER PUBLICATIONS

Karcher H: Three–dimensional craniofacial surgery: transfer from a three–dimensional (Endoplan) to clinical surgery: a new technique (Graz). J Craniomaxillofac Surg 20:125, 1992.

Okumura H, Chen LH, Tsutsumi S, et al: Three–dimensional virtual imaging of facial skeleton and dental morphologic condition for treatment planning in orthognathic surgery. AM J Orthodont Dentofac Orthoped 116:126, 1999.

Santler G: The Graz hemisphere splint: a new precise, non–invasive method of replacing the dental arch of 3D–models by plaster models. J Craniomaxillofac Surg 27:169, 1999.

Terai H, Shimahara M, Sakinaka Y, et al: Accuracy of integration of dental casts in three–dimensional models (with discussion). J Oral Maxillofac Surg 57:662, 1999.

* cited by examiner

Primary Examiner—Ruth S. Smith
(74) Attorney, Agent, or Firm—Loren G. Helmreich; Bowning Bushman, P.C.

(57) ABSTRACT

A method of forming a surgical splint to receive a patient's dentition and thereby align the upper jaw and the lower jaw during surgery includes generating a CT computer model of bone structure, generating a digital dental computer model of the patient's dentition, and then combining the CT computer model and the digital dental computer model to form a composite computer model. The composite computer model may be displayed, and at least one of the upper jaw and lower jaw repositioned relative to the patient's skull and the composite computer model to form a planned position computer model. Using this desired position computer model, a computer model surgical splint of the patient's dentition may be formed, which is then input into a fabrication machine to form a surgical splint. The method also includes forming and displaying the composite computer model. A workstation includes a CT machine, a digital scanner, a computer, an input command mechanism, a display, and a fabricating machine.

18 Claims, 6 Drawing Sheets

METHOD AND APPARATUS FOR FABRICATING ORTHOGNATHIC SURGICAL SPLINTS

FIELD OF THE INVENTION

The present invention relates to equipment and methods to fabricate orthognathic surgical splints, and to a related technique for creating a computerized composite skull model useful for diagnosis and treatment planning.

BACKGROUND OF THE INVENTION

Surgical planning for orthognathic surgery traditionally combines various diagnostic methods to achieve the final surgical plan. Anthropometric measurements are manually taken on the patient at clinical examinations. Cephalometric radiographs are analyzed with angular and linear measurements. Facial aesthetics are evaluated by direct visual inspection and photography. Plaster dental models are conventionally used to analyze patient's dentition. Video imaging techniques may be used to estimate the movements resulting from the surgery and to predict soft tissue changes. Used together, these diagnostic methods allow the clinicians to plan surgical movements of the patient's jaws and teeth in all dimensions.

Figure 1:
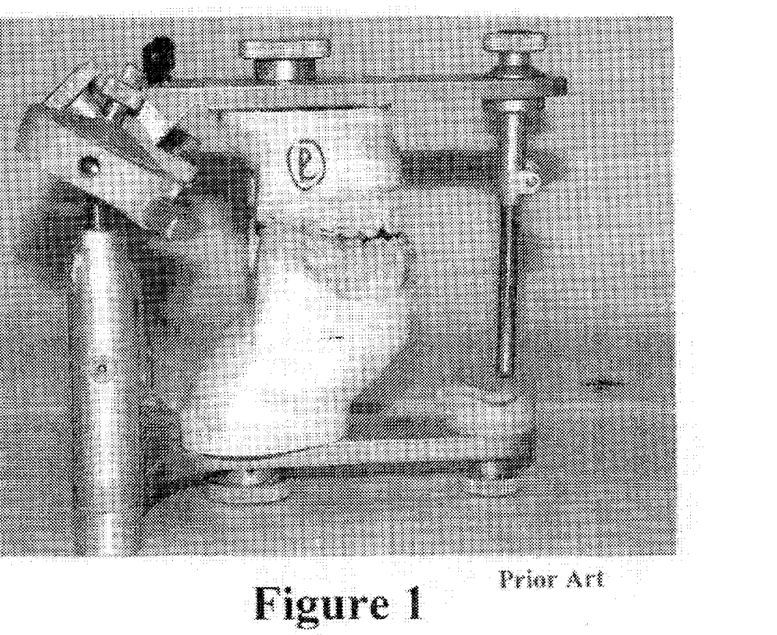
FIG. 1 is a photograph of a conventional plaster dental model mounted on articulators.

As indicated above, plaster dental models are conventionally used to replicate the patient's teeth. Since plaster dental models lack bony support, these models are of limited value because the clinicians cannot visualize the surrounding bony structures, which are critical to the treatment of complex cranio-maxillofacial deformities. A conventional plaster dental model mounted on articulators is shown in FIG. 1.

Surgical splints fabricated from plaster dental models nevertheless are used to transfer the treatment plan to the patient in the operating room. The thin acrylic splint contains indentations of the incisal edges and cusps of the teeth, and ideally provides for precise positioning of the upper jaw relative to the lower jaw. Most commonly, intermediate splints are used to position an osteotomized maxilla to an uncut mandible, and final splits are used to align the mandible to the repositioned maxilla. The problem remains that the splints fabricated from the plaster dental models do not properly position the jaws relative to the remaining structure of the skull.

Clinicians have attempted to create physical skull models which depict both the patient's bone structure and dentition. Several investigators have attempted to incorporate plaster dental models into physical milled stereolithographic skull models, as indicated in an article published in J Oral Maxillofac Surg, Volume 77, page 662. A physical skull model with a plaster dental model mounted on articulators may cost $2,000.00 or more. Various other publications discuss the creation of physical composite skull models. Since all these methods are based on creating physical models, the high cost and limited flexibility of the models have highly restricted their use.

The disadvantages of the prior art are overcome by the present invention, and improved methods and apparatus are hereinafter disclosed for fabricating stereolithographic orthognathic surgical splints from digital dental models, and for combining digital dental models with three-dimensional computed tomography (CT) models.

SUMMARY OF THE INVENTION

According to a preferred embodiment of the invention, a computerized treatment plan for each patient involves the creation of one or more stereolithographic surgical splints. These splints are computer generated and digitally fabricated, and are therefore highly accurate. According to the present invention, diagnosis, surgical planning and simulation, and the fabrication of surgical splints may be accomplished using a computer and an SLA machine. Accordingly, patients with craniofacial and maxillofacial facial deformities may be scanned to obtain three-dimensional CT data, and their dentition may be laser scanned. Computerized virtual osteotomies may be performed on a computerized CT skull model, and the treatment plan may be transferred to the patient through the intermediate and final surgical splints, which are computer generated and then digitally fabricated. The techniques of the present invention for generating surgical splints may replace traditional plaster dental model surgery, as discussed above.

The computerized composite skull model of the present invention combines three-dimensional CT bone model data with digital dental model data. The composite skull model may be used for accurate visualization during diagnosis and treatment planning. The computerized composite skull model may be used to generate a stereolithographic model of the patient's craniofacial skeleton and dentition, and may be used to improve surgical outcomes with reduced operating time.

It is an object of the present invention to provide an improved process for forming a surgical splint which will receive a patient's dentition and thereby properly align both the upper and lower jaw relative to the patient's skull. A three dimensional computed tomography model of bone structure for the patient's upper jaw, lower jaw, and at least a portion of the skull may be generated. A digital dental computer model may also be generated of the patient's dentition utilizing laser surface scanning. The computed tomography computer model and the digital dental computer model may then be combined to form a composite computer model. The two models may be aligned utilizing fiduciary markers. The composite model may then be displayed, and the clinician may reposition at least one of the upper and the lower jaw relative to the patient's skull to form a planned position computer model. Using this planned position computer model, a computer model surgical splint may be formed. The computer model surgical splint may then used to generate a physical surgical splint.

It is a feature of the present invention that the composite computer model may be used by the clinician in various ways to assist in diagnosis, surgical planning, and simulation of surgical outcomes.

A significant feature of the present invention is that highly reliable positioning of the upper jaw and lower jaw relative to the skull is obtained using a surgical splint which is manufactured using a combination of the CT model data and the digital dental model data.

A significant advantage of the present invention is that the substantial costs and limited flexibility of plaster dental models and stereolithographic skulls models may be voided.

These and further objects, features, and advantages of the invention will become apparent from the following detailed description wherein reference is made to the figures in the accompanying drawings.

DETAILED DESCRIPTION OF PREFERRED EMBODIMENTS

The present invention incorporates a digital dental model into a three-dimensional CT model, thereby obtaining a computerized composite skull model of both the highly accurate bone information obtained by the CT process and the accurate digital dental model data.

Figure 2:
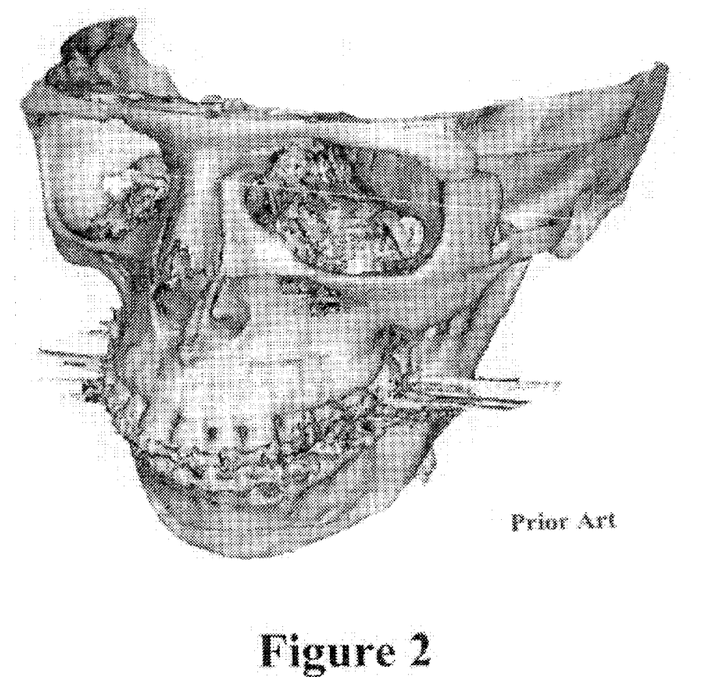
FIG. 2 is a photograph of a three-dimensional CT image.

Three-dimensional CT models as shown in FIG. 2 have been used in craniofacial and maxillofacial surgery, since CT imaging provides an excellent representation of bone structure. CT scanners capture images layer by layer, and data between the image layers is conventionally reconstructed by mathematical algorithms. A significant disadvantage of CT, however, is that it is not capable of accurately representing the teeth. A scattering of the CT image as shown in FIG. 2 may be due to orthodontic metal brackets, dental fillings, or prosthesis. The technique of the present invention creates a three-dimensional computerized composite skull model which represents both the fine bony structures and precise dental structures. Using this model, diagnosis and treatment planning may be significantly improved.

Figure 3:
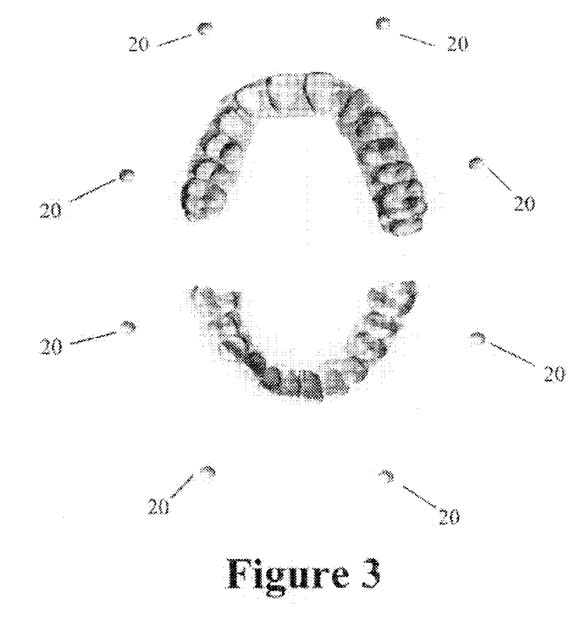
FIG. 3 is a photograph of a set of digital dental models with fiduciary markers, which may be arranged as shown in FIG. 4.
Figure 4:
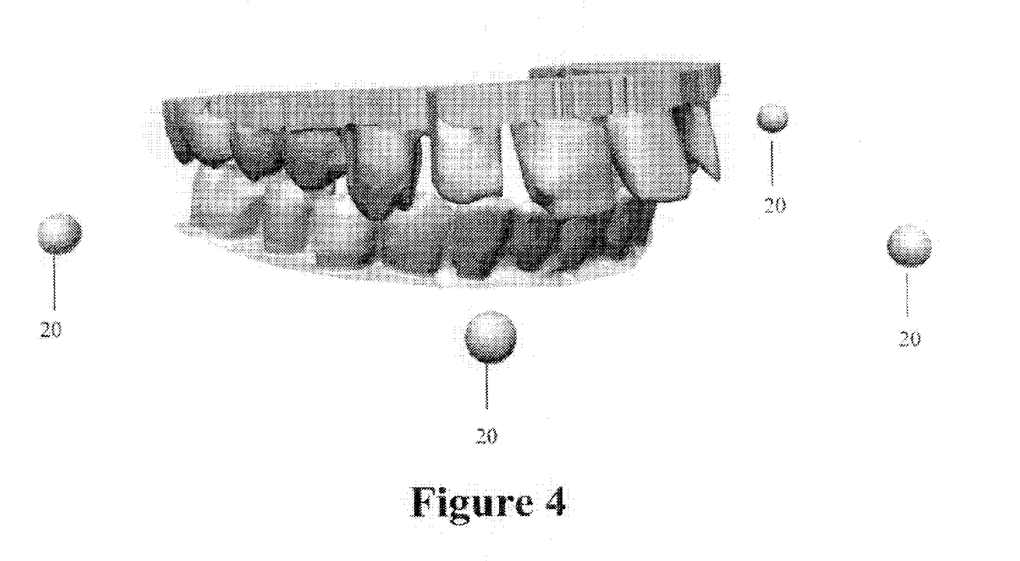
Figure 9:
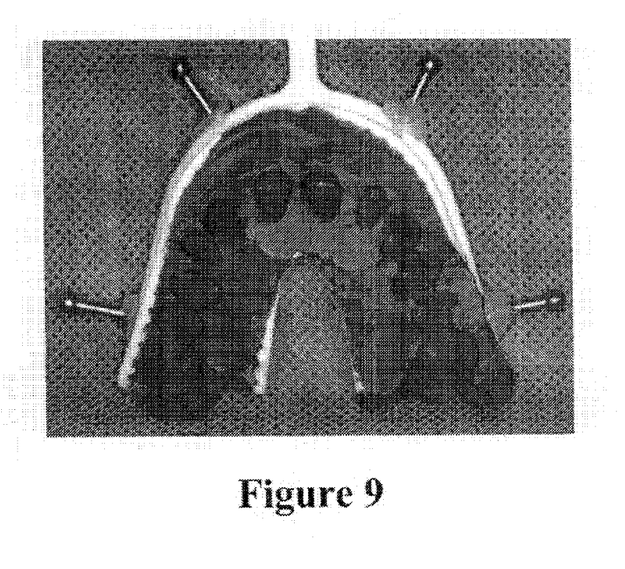
FIG. 9 is a photograph of a triple tray with four fiduciary members subsequent to making upper and lower dental impressions.

To form the composite skull model of the present invention, a set of digital dental models as shown in FIG. 3 may be made on the patient's dentition in a conventional manner, but with the addition of fiduciary markers 20. The digital dental models may then be positioned as shown in FIG. 4. Digital dental models may be conventionally obtained by laser surface scanning of the dental impressions. The fiduciary markers may be inserted into the radiolucent full-arch dental impression tray, as shown in FIG. 9. Titanium balls may be used as suitable fiduciary markers. A triple-tray may be used to take simultaneous impressions of the maxillary and mandibular arches. Four fiduciary markers may be mounted on the tray, with one pair for the left and right canine region, and the other pair for the left and right molar region. The dental impressions with the four fiduciary markers may be scanned using a 3-D laser surface scanner to obtain the digital dental model. The digital dental model provides for highly accurate occlusion relationships.

Figure 5:
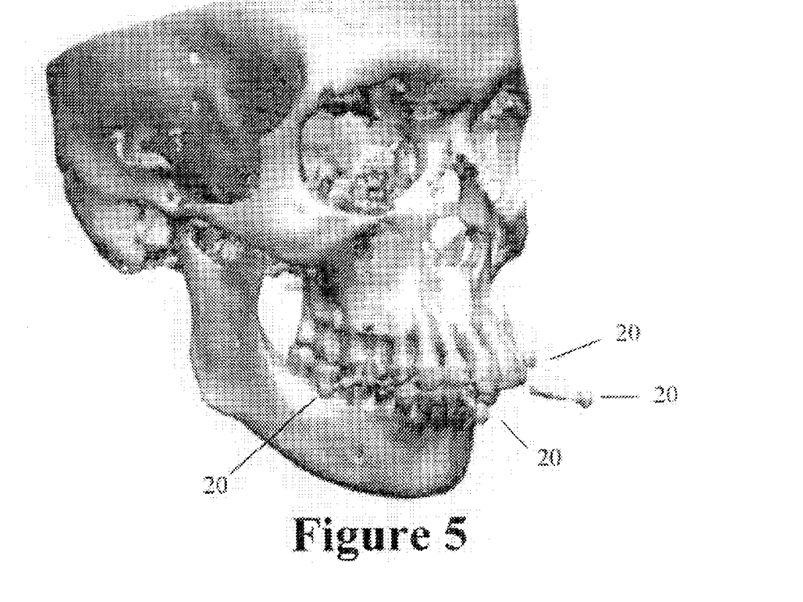
FIG. 5 illustrates a three-dimensional CT skull model with fiduciary markers.
Figure 6:
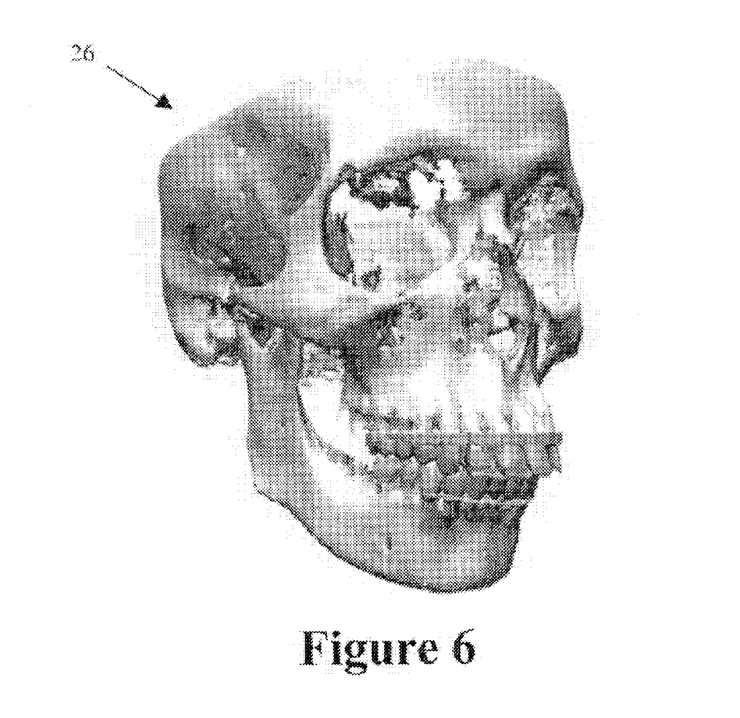
FIG. 6 illustrates a computerized composite skull model.

A three-dimensional CT bone model of the skeleton may be taken on the same patient with the same set of fiduciary markers, as shown in FIG. 5. The CT skull model is constructed from the CT scan of the skull. Using computer programming, the four fiduciary markers may be located in the same position for both the CT data and the digital dental model data. Interactive alignment of the corresponding fiduciary markers thus provides alignment between the bone model and the digital dental model. The fiduciary markers may then be removed to create a precise composite of the skull model 26, as shown in FIG. 6. By incorporating the digital dental model into the CT skull model through alignment of the fiduciary markers, a highly accurate computerized composite skull model may be obtained. Digital dental model information is incorporated into the computerized CT bone model to accurately represent both bony structures and teeth. By establishing the dental occlusion, it is possible to precisely formulate a computerized surgical plan and simulate outcomes prior to surgery. Treatment planning with the composite model may replace the need for traditional plaster dental models, and will help the surgeon reduce operative time and improve surgical outcomes.

The composite computer model may be displayed, so that one or both of the upper jaw and the lower jaw are selectively repositioned relative to the skull to a planned position computer model. With the computer model, surgeons may move and rotate bone segments to any desired position. Recognizing that the lower jaw "floats" with respect to the skull and the upper jaw, the upper and lower jaws may be positioned in the composite computer model so that the jaws come together with desired alignment of the jaws and the dentition. Using the upper and lower jaw planned position computer model, the dental splint may be formed to receive the teeth. The computerized composite skull model may thus be used to generate a stereolithographic model of the patient's craniofacial skeleton and dentition. The techniques of the present invention allow a surgical plan to be employed which includes a digital dental model to establish the occlusion and fabricate surgical splints. Using the composite CT model of the present invention, surgical planning will thus be optimized to produce the desired surgical outcome.

Figure 7:
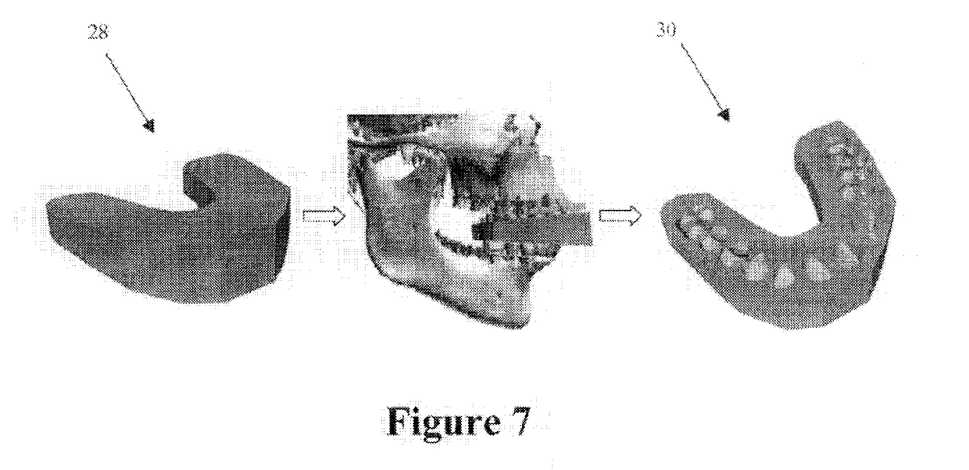
FIG. 7 is an illustration of the process according to the present invention for fabricating a surgical splint.

After the digital dental model as shown in FIG. 4 has been incorporated into the CT model as shown in FIG. 5 to produce the computerized composite model 26 as shown in FIG. 6, a computerized horseshoe wafer 28 may be generated, as shown in FIG. 7. This wafer may then be placed between the digital maxillary and mandibular dental arches of the computerized composite skull model, and the lower jaw moved to indent the wafer with both the upper and lower teeth. After Boolean operations to subtract the teeth from the wafer, it produces a digital dental splint 30. A physical dental splint 32 may then be fabricated with the SLA machine using the digital dental splint 30 as a model. The treatment plan may thus be transferred from the computer to the patient to form both intermediate and final surgical splints generated according to the techniques of the present invention.

To test the accuracy of the composite model of the present invention, a complete dry skull was used to generate a composite skull model, with both CT bone and digital dental data. On the computerized skull model, three-dimensional measurements were taken between bones and between teeth, and from bone to tooth. These same dimensions were manually taken from the dry skull. The results indicate that the computerized composite model accurately represented bone structures from the CT data, but also reproduced accurate dentition from the digital models.

Figure 8:
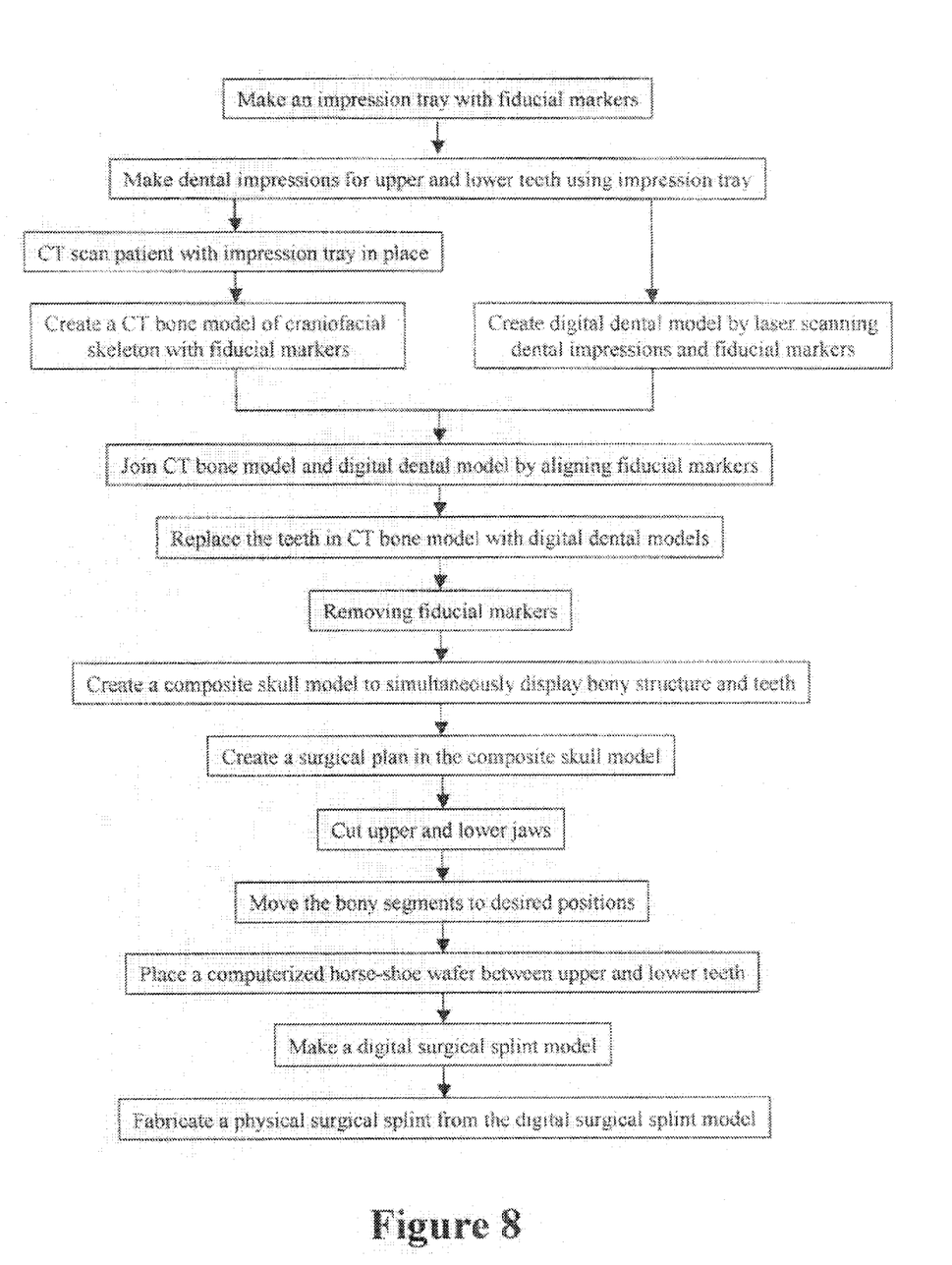
FIG. 8 is a more specific flow chart of the process for forming a surgical splint.

FIG. 8 is a block diagram of a suitable process according to the present invention for fabricating a surgical splint. As discussed above, impressions of the dentition may be made for both upper and lower teeth using an impression tray, with fiduciary markers secured to the tray. Using the dental impression tray, a digital dental model may be obtained by laser scanning the dental impressions with the fiduciary markers in place. Using the same dental tray and with the fiduciary markers in place, a CT scan of the patient may be obtained to create a CT bone model of the craniofacial skeleton with the fiduciary markers in place. The CT bone model, which is highly accurate in depicting bone structure, is then combined with the digital dental model, which accurately depicts the dentition, by alignment of the fiduciary markers. The teeth in the CT bone model are thus replaced with the digital dental model, so that when the fiduciary markers are removed a composite skull bone model is created which accurately displays both the bony structure and the teeth.

Using this composite skull model, a surgical plan may be developed. In many applications, that plan will include making one or more cuts in the upper jaw or lower jaw, so that the bony segments of the jaw may be moved to desired positions. Once a selected position is obtained, a computerized pressure horseshoe-shaped wafer may be placed between the upper and lower teeth to fabricate a digital surgical splint model, as shown in FIG. 7. Using the digital surgical splint model, a physical surgical splint may be generated using an SLA machine.

According to a preferred embodiment of the invention, a stereolithographic apparatus (SLA machine) is preferably used to fabricate the dental splint from the computer model surgical splints. It should be understood, however, that various types of computer controlled rapid prototype machines may be used for accurately fabricating surgical splints once supplied with the proper surgical splint computer information.

To test the accuracy of the technique for forming surgical splints according to the present invention, a surgical splint was fabricated for each of a number of volunteers. One stereolithographic and one conventional acrylic splint was generated for each volunteer. The air space between the teeth and the splint was quantified. The air spaces were recorded by impression materials and sliced cross-sectionally. Corresponding areas of the cross-sectional airspaces between the stereolithographic and the acrylic splints were then measured and compared. The results indicated that the techniques of the present invention were highly accurate.

According to the present invention, diagnosis, surgical planning and simulation, and surgical splint fabrication may be accomplished at the computer and computerized splint fabrication machine. Patients with craniofacial and maxillofacial deformities may be CT scanned, and their dentition may be laser scanned. Computerized virtual osteotomies may be performed on the computerized skull model, and the treatment plan transferred from the computer to the patient through the intermediate and final surgical splints. Accordingly, traditional plaster dental model surgery may be replaced by the more cost effective and versatile techniques of the present invention.

Figure 10:
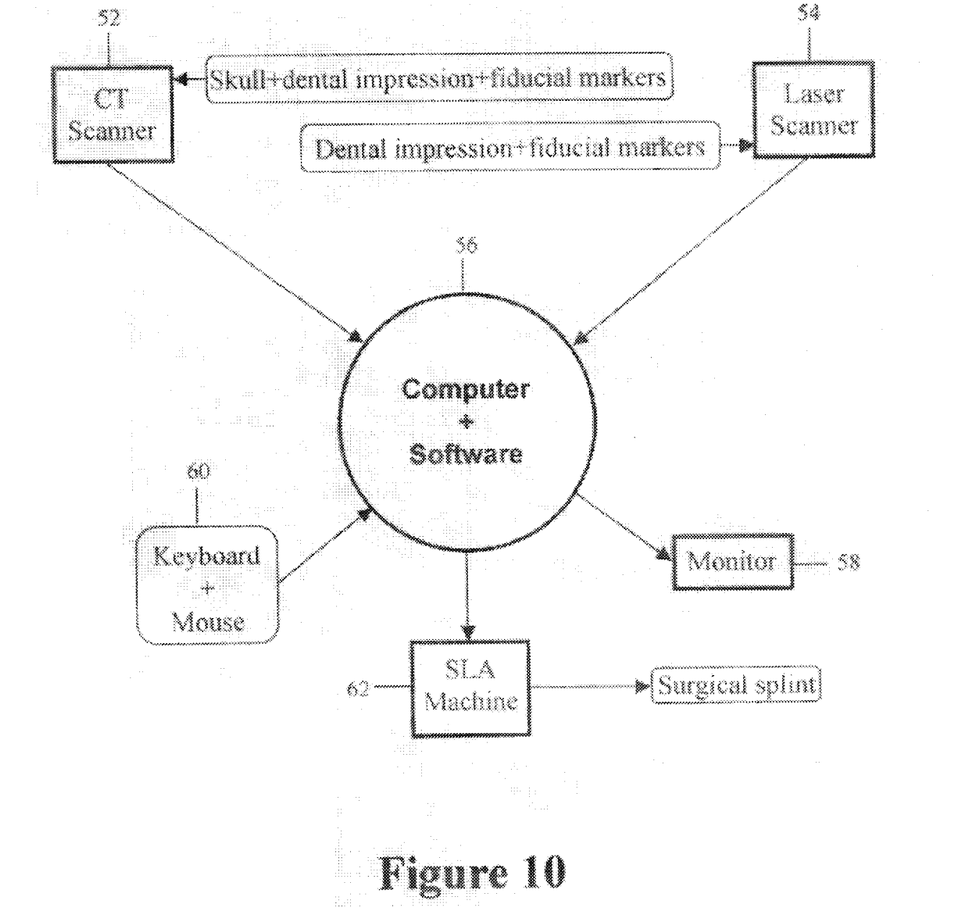
FIG. 10 schematically depicts the major components of a workstation according to the present invention.

A desired workstation according to the present invention is shown in FIG. 10 and preferably includes the components required to form the computerized composite models and the surgical splints. The workstation 50 includes a CT scanner machine 52, a scanner 54 for obtaining a digital dental model, and a computer with software 56 for combining the data from the CT machine and the digital dental scanner. Software for aligning the digital markers and for creating the computerized horseshoe wafer may be obtained commercially from various sources, including Discrete, Inc. in Montreal, Canada, marketed as 3D Studio Max. A screen, monitor 58 or other device displays the composite model. A keyboard, mouse, or other input command mechanism 60 to the computer allows the clinician to reposition at least one of the upper jaw and the lower jaw relative to the patient's skull to form the desired position computer model. Using this desired position computer model, a computer model surgical splint may be generated, and the data from the computer model surgical splint then input into an SLA machine or another computer-based manufacturing machine 62 for fabricating a surgical splint. With the improved surgical splint, teeth on the patient may be positioned within the splint, and plates, screws, and other mechanisms then conventionally used to fix the upper and lower jaw in place during the surgical technique.

While preferred embodiments of the present invention have been illustrated in detail, it is apparent that modifications and adaptions of the preferred embodiments will occur to those skilled in the art. However, it is to be expressly understood that such modifications and adaptations are within the spirit and scope of the present invention as set forth in the following claims.

What is claimed:

1. A method of forming a surgical splint to receive a patient's dentition and thereby align the upper jaw and the lower jaw relative to the patient's skull during surgery, comprising:

generating a three-dimensional computed tomography computer model of bone structure for the patient's upper jaw, lower jaw, and at least a portion of the patient's skull;

generating a digital dental computer model of the patient's dentition;

positioning a plurality of fiduciary markers relative to the patient's dentition identifiable in both the digital dental computer model and the computed tomography computer model;

combining the computed tomography computer model and the digital dental computer model to form a composite computer model with the fiduciary markers aligned;

displaying the composite computer model;

repositioning at least one of the upper jaw and the lower jaw relative to the patient's skull in the composite computer model to form a planned position computer model;

using the desired position computer model, forming a computer model surgical splint of the patient's dentition; and forming the surgical splint from the computer model surgical splint.

2. The method as defined in claim 1, wherein at least two fiduciary markers are positioned with respect to the canine region of the patient's dentition and at least two other fiduciary markers are positioned with respect to the molar region of the patient's dentition.

3. The method as defined in claim 1, wherein forming the computer model surgical splint comprises:

providing a computerized wafer;

positioning the computerized wafer between the upper dentition and the lower dentition in the desired position computer model; and forming the computer model surgical splint by impressing the dentition on the computerized wafer.

4. A method as defined in claim 3, wherein the wafer is placed between the digital maxillary and mandibular dental arches of the composite computer model, and the lower jaw is moved to indent the wafer with upper and lower teeth.

5. A method as defined in claim 4, wherein indentions in the wafer formed by the teeth are digitized to produce the splint.

6. The method as defined in claim 1, wherein the digital dental computer model is formed by laser surface scanning the patient's dentition.

7. The method as defined in claim 1, wherein the surgical splint is formed using a stereolithographic apparatus.

8. A method of forming a composite computer model of a patient's bone structure and dentition, comprising:

positioning a plurality of fiduciary markers relative to the patient's dentition;

generating a three-dimensional computed tomography computer model of the patient's bone structure and the fiduciary markers for the patient's upper jaw, lower jaw, and at least a portion of the patient's skull;

generating a digital dental computer model of the patient's dentition and the fiduciary markers;

combining the computed tomography computer model and the digital dental computer model by aligning the fiduciary markers to form a composite computer model; and     displaying the composite computer model.

9. The method as defined in claim 8, further comprising:

repositioning at least one of the upper jaw and the lower jaw relative to the patient's skull in the composite computer model to form a desired position computer model.

10. The method as defined in claim 9, further comprising:

using the desired position computer model, forming a computer model surgical splint of the patient's dentition.

11. The method as defined in claim 10 wherein forming the computer model surgical splint comprises:

providing a computerized wafer;

positioning the computerized wafer between the upper dentition and the lower dentition in the desired position computer model; and     forming the computer model surgical splint by impressing the dentition on the computerized wafer.

12. A method as defined in claim 11, wherein the wafer is placed between the digital maxillary and mandibular dental arches of the composite computer model, and the lower jaw is moved to indent the wafer with upper and lower teeth.

13. The method as defined in claim 8, wherein the digital dental model is formed by laser surface scanning the patient's dentition.

14. The method as defined in claim 8, wherein at least two fiduciary markers are positioned with respect to the canine region of the patient's dentition and at least two other fiduciary markers are positioned with respect to the molar region of the patient's dentition.

15. A workstation for forming a surgical splint to receive a patient's dentition and thereby align both the upper jaw and the lower jaw relative to the patient's skull during surgery, comprising:

a three-dimensional computed tomography machine for generating a CT model of bone structure for the patient's upper jaw, lower jaw, and at least a portion of the patient's skull;

a digital scanner for generating a digital dental computer model of the patient's dentition;

a plurality of fiduciary markers for positioning relative to the patient's dentition;

a computer for combining the CT computer model and the digital dental computer model to form a composite computer model with the fiduciary markers aligned;

an input command mechanism for repositioning at least one of the upper jaw and the lower jaw relative to the patients skull to form a desired position computer model;

a display for displaying the desired position computer model; and     a fabricating machine for inputting the desired position computer model data to fabricate a surgical splint.

16. The workstation as defined in claim 15, wherein at least two fiduciary markers are provided for positioning with respect to the canine region of the patient's dentition and at least two other fiduciary markers are provided for positioning with respect to the molar region of the patient's dentition.

17. The workstation as defined in claim 15, wherein the fabricating machine/comprises a stereolithographic apparatus.

18. The workstation as defined in claim 15, wherein the digital scanner comprises a laser surface scanner.

\* \* \* \* \*